(12) United States Patent
Chen et al.

(10) Patent No.: US 9,003,755 B2
(45) Date of Patent: Apr. 14, 2015

(54) METHOD AND APPARATUS FOR MEASURING REFLECTIVE INTENSITY OF DISPLAY SURFACE

(71) Applicant: Shenzhen China Star Optoelectronics Technology Co., Ltd., Shenzhen, Guangdong (CN)

(72) Inventors: Lixuan Chen, Shenzhen (CN); Chih-tsung Kang, Shenzhen (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 177 days.

(21) Appl. No.: 13/813,437

(22) PCT Filed: Jan. 24, 2013

(86) PCT No.: PCT/CN2013/070939
§ 371 (c)(1),
(2) Date: Jan. 31, 2013

(87) PCT Pub. No.: WO2014/107925
PCT Pub. Date: Jul. 17, 2014

(65) Prior Publication Data
US 2014/0198316 A1 Jul. 17, 2014

(30) Foreign Application Priority Data
Jan. 12, 2013 (CN) .......................... 2013 1 0011303

(51) Int. Cl.
*G01N 21/55* (2014.01)
*G09G 3/00* (2006.01)

(52) U.S. Cl.
CPC ............... *G09G 3/006* (2013.01); *G01N 21/55* (2013.01); *G01N 2201/0616* (2013.01)

(58) Field of Classification Search
CPC ......... G09G 3/32; G09G 3/20; G09G 3/2011; G09G 5/00; G09G 5/10; G09G 3/36; G01M 11/00; G01B 11/26; G01N 21/55; G01N 21/474; G01N 21/57; G01N 21/274; G01N 21/86
USPC ............. 356/448; 345/207, 690, 581, 102, 82
See application file for complete search history.

(56) References Cited

U.S. PATENT DOCUMENTS

| | | | | |
|---|---|---|---|---|
| 2006/0274027 A1* | 12/2006 | Yamaguchi | .................... | 345/102 |
| 2007/0055143 A1* | 3/2007 | Deroo et al. | .................. | 600/425 |
| 2010/0259555 A1* | 10/2010 | Hibi et al. | ..................... | 345/601 |
| 2011/0261039 A1* | 10/2011 | Kubota | .......................... | 345/207 |
| 2012/0268350 A1* | 10/2012 | Yoshimura | .................... | 345/1.3 |

* cited by examiner

*Primary Examiner* — Tarifur Chowdhury
*Assistant Examiner* — Isiaka Akanbi
(74) *Attorney, Agent, or Firm* — Andrew C. Cheng

(57) ABSTRACT

The present invention provides a method for measuring reflective intensity of display surface, including: obtaining a luminance value of a first display and a luminance value of a second display when displaying, the first display and the second display having the same observed luminance, the peripheral of the surface of the first display being surrounded by light-shielding object, the first display and the second display being placed side by side; and obtaining the reflective intensity of the display surface in the ambient based on the luminance value of the first display and the luminance values of the second display when displaying. As such, the present invention provides convenient and accurate means to measure the reflective intensity of display surface.

11 Claims, 3 Drawing Sheets

S101 obtaining luminance values of first display and second display when displaying in the same ambient.

S102 obtaining the reflective intensity of the display surface in the ambient based on luminance values of the first display and the second display.

METHOD AND APPARATUS FOR MEASURING REFLECTIVE INTENSITY OF DISPLAY SURFACE

BACKGROUND OF THE INVENTION

1. Field of the Invention

The present invention relates to the field of visual measuring techniques, and in particular to a method and apparatus for measuring reflective intensity of display surface.

2. The Related Arts

The majority of displays of various equipments are reflective to various degrees. When the equipment is used in a bright working ambient, the surface of the equipment display will be affected by the reflection of the ambiental light and result in poor readability.

Therefore, it is imperative to know the reflective intensity of the display surface so as to adjust the luminance of the display in order to improve the readability. The known method for measuring the luminance is usually by a luminance meter. However, the luminance meter is unable to directly measure the reflective intensity of the surface of a visual perception-based display operating in a bright ambient. Other measuring means often requires auxiliary equipments, which is often inaccessible or difficult to operate by the user.

SUMMARY OF THE INVENTION

The technical issue to be addressed by the present invention is to provide a method and apparatus for measuring reflective intensity of a display surface, providing convenient and accurate measurement of reflective intensity on the display surface.

The present invention provides a method for measuring reflective intensity of display surface, which comprises: placing a first display and a second display in the same ambient, dividing the display luminance of the second display into N levels, wherein N being an integer greater than 1, placing light-shielding object to surround the peripheral of surface of the first display, the first display and the second display being placed side by side; at a luminance level of the N luminance levels of the second display, adjusting the display luminance of the first display so that the first display and the second display having the same observed luminance; using a luminance meter to press against the surface of the second display to obtain a luminance value L2 for each of N luminance levels of the second display, and using a luminance meter to press against the surface of the first display to obtain a corresponding luminance value L1 of the first display when the first display and the second display having the same observed luminance; obtaining the reflective intensity of the display surface in the ambient based on the luminance value of the first display and the luminance values of the second display when displaying.

According to a preferred embodiment of the present invention, the step of obtaining the reflective intensity of the display surface in the ambient based on the luminance value of the first display and the luminance values of the second display when displaying further comprises: for each luminance level of the second display, computing the difference between the luminance value L2 of the second display and the luminance value L1 of the first display; and computing an average of the differences between the luminance value L2 of the second display and the corresponding luminance value L1 of the first display of all the N luminance levels, wherein the average being the reflective intensity of the display surface in the ambient.

According to a preferred embodiment of the present invention, the surface of the first display and the surface of the second display are made of the same material.

The present invention provides a method for measuring reflective intensity of display surface, which comprises: obtaining a luminance value of a first display and a luminance value of a second display when the first display and the second display displaying, the first display and the second display having the same observed luminance, the peripheral of the surface of the first display being surrounded by light-shielding object, the first display and the second display being placed side by side; and obtaining the reflective intensity of the display surface in the ambient based on the luminance value of the first display and the luminance values of the second display when displaying.

According to a preferred embodiment of the present invention, the step of obtaining a luminance value of a first display and a luminance value of a second display when the first display and the second display displaying further comprises: dividing the display luminance of the second display into N levels, wherein N being an integer greater than 1; at a luminance level of the N luminance levels of the second display, adjusting the display luminance of the first display so that the first display and the second display having the same observed luminance; and obtaining a luminance value L2 for each of N luminance levels of the second display and obtaining a corresponding luminance value L1 of the first display when the first display and the second display having the same observed luminance.

According to a preferred embodiment of the present invention, the step of obtaining the reflective intensity of the display surface in the ambient based on the luminance value of the first display and the luminance values of the second display when displaying further comprises: for each luminance level of the second display, computing the difference between the luminance value L2 of the second display and the luminance value L1 of the first display; and computing an average of the differences between the luminance value L2 of the second display and the corresponding luminance value L1 of the first display of all the N luminance levels, wherein the average being the reflective intensity of the display surface in the ambient.

According to a preferred embodiment of the present invention, the step of obtaining a luminance value of a first display and a luminance value of a second display when the first display and the second display displaying further comprises: in the same ambient, using a luminance meter to press against the surfaces of the first display and the second display to obtain a luminance value of the first display and a luminance value of the second display when displaying.

According to a preferred embodiment of the present invention, the surface of the first display and the surface of the second display are made of the same material.

The present invention provides an apparatus for measuring the reflective intensity of display surface, which comprises: a luminance obtaining module, configured to obtain a luminance value of a first display and a luminance of a second display displaying in the same ambient wherein the first display and the second display having the same observed luminance, the peripheral of the surface of the first display being surrounded by light-shielding object, the first display and the second display being placed side by side; a reflective intensity obtaining module, configured to obtain the reflective intensity of the display surface in the ambient based on the luminance value of the first display and the luminance values of the second display when displaying.

According to a preferred embodiment of the present invention, the luminance obtaining module further comprises: a dividing unit, configured to divide the display luminance of the second display into N levels, wherein N being an integer greater than 1; an adjusting unit, configured to adjust, at a luminance level of the N luminance levels of the second display, the display luminance of the first display so that the first display and the second display having the same observed luminance; and an obtaining unit, configured to obtain a luminance value L2 for each of N luminance levels of the second display, and obtain a corresponding luminance value L1 of the first display when the first display and the second display having the same observed luminance.

According to a preferred embodiment of the present invention, the reflective intensity obtaining module comprises: a difference computing unit, configured to compute, for each luminance level of the second display, the difference between the luminance value L2 of the second display and the luminance value L1 of the first display; and an average computing unit, configured to compute an average of the differences between the luminance value L2 of the second display and the corresponding luminance value L1 of the first display of all the N luminance levels, wherein the average being the reflective intensity of the display surface in the ambient.

According to a preferred embodiment of the present invention, the luminance obtaining module is, specifically, in the same ambient, using a luminance meter to press against the first display and the second display to obtain the luminance value of the first display and the luminance value of the second display when displaying.

According to a preferred embodiment of the present invention, the surface of the first display and the surface of the second display are made of the same material.

The efficacy of the present invention is that to be distinguished from the state of the art. Under the circumstance of the first display and the second display having the same observed luminance, the present invention obtains the luminance values of the first display and the second display placed in the same ambient, wherein the peripheral of the surface of the first display is surrounded by light-shielding object to effectively shield the ambient light to reduce or eliminate the effect on the measurement so as to obtain the luminance value of the first display in the state of free of ambient light effect or near free of ambient light effect, and obtain the luminance of the second display in the same ambient under the effect of the ambient light. Then, based on the luminance values of the first display and the second display, the present invention computes the reflective intensity of the display surface in the ambient. The present invention provides convenient and accurate means to measure the reflective intensity of the display surface without extra equipments and extra cost.

BRIEF DESCRIPTION OF THE DRAWINGS

To make the technical solution of the embodiments according to the present invention, a brief description of the drawings that are necessary for the illustration of the embodiments will be given as follows. Apparently, the drawings described below show only example embodiments of the present invention and for those having ordinary skills in the art, other drawings may be easily obtained from these drawings without paying any creative effort. In the drawings.

DETAILED DESCRIPTION OF THE PREFERRED EMBODIMENTS

The following refers to drawings and the embodiment to describe the present invention in details.

Figure 1:
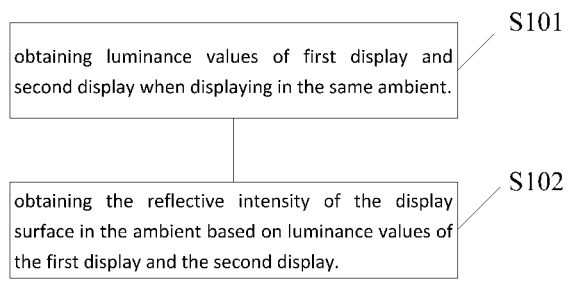
FIG. 1 is a flowchart of a method for measuring reflective intensity of display surface according to the present invention.

Referring to FIG. 1, FIG. 1 is a flowchart of a method for measuring reflective intensity of display surface according to the present invention.

Step 101: obtaining a luminance value of a first display and a luminance value of a second display when the first display and the second display displaying, the first display and the second display having the same observed luminance, the peripheral of the surface of the first display being surrounded by light-shielding object, the first display and the second display being placed side by side.

The display of the current display device often uses material with certain reflectivity, such as, glass. The first display and the second display of the present invention can be displays of known display device. The observed luminance can be the luminance perceived by the human eye at a certain distance, for example, 2.5 m, in front of the first and the second display. As the observed value is not absolute objective in a single iteration, a plurality of observed luminance values can be obtained to improve the accuracy.

By placing the first display and the second display side by side in a bright ambient, such as, an ambient lit by bright fluorescent light or in a bright office, and surrounding the peripheral of the display surface of the first display with light-shielding object, such as, light-shielding board, the effect of the ambient light can be effective reduced or eliminated. When the first display and the second display have the same observed luminance, the luminance value of the first display and the luminance value of the second display in the bright ambient are obtained.

Step 102: obtaining the reflective intensity of the display surface in the ambient based on the luminance value of the first display and the luminance values of the second display when displaying.

In an idealistic situation, the luminance value of the first display when displaying is not affected by the ambient light. The present invention uses the light-shielding objects to surround the peripheral of the surface of the first display to achieve the state that is free of the ambient light effect or near free of the ambient light effect, while the second display is not surrounded by the light-shield objects. In a bright ambient, based on the luminance value of the first display and the luminance values of the second display when displaying, the present invention obtaining the reflective intensity of the display surface in the ambient through computation.

Figure 2:
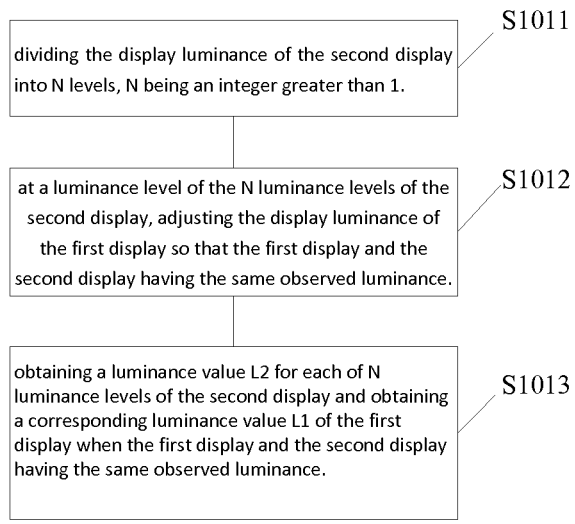
FIG. 2 is a flowchart of obtaining the reflective intensity of the display surface in the ambient based on the luminance value of the first display and the luminance values of the second display when displaying in the method for measuring reflective intensity of display surface according to the present invention.

Referring to FIG. 2, FIG. 2 is a flowchart of obtaining the reflective intensity of the display surface in the ambient based on the luminance value of the first display and the luminance values of the second display when displaying in the method for measuring reflective intensity of display surface according to the present invention, comprising the following steps.

Step S1011: dividing the display luminance of the second display into N levels, wherein N being an integer greater than 1.

The display luminance of the second display is divided into N levels, wherein the level 1 is the darkest and the level N is the brightest, N is an integer greater than 1. The more levels are divided, the more refined the display quality is. For human eye, the luminance can be roughly divided into 7 levels, i.e., white, gray-white, light gray, gray, dark gray, light black and black. However, with the aid of measure equipment, the grayscale can be further divided. Specifically, the grayscale of a typical display is 256 levels, with each grayscale level representing a different luminance level. The present invention does not impose any specific restriction on the division levels.

Step S1012: at a luminance level of the N luminance levels of the second display, adjusting the display luminance of the first display so that the first display and the second display having the same observed luminance.

At a luminance level of the N luminance levels of the second display, adjust the display luminance of the first display and compare the display luminance of the two displays so that the first display and the second display have the same observed luminance. At this point, the luminance level of the first display and the second display can be considered corresponding level. Because different materials have different reflectivity, the first display and the second display of the present embodiment are made of the same material.

Step S1013: obtaining a luminance value L2 for each of N luminance levels of the second display and obtaining a corresponding luminance value L1 of the first display when the first display and the second display having the same observed luminance.

Obtaining a luminance value L2 for each of N luminance levels of the second display and obtaining a corresponding luminance value L1 of the first display when the first display and the second display having the same observed luminance, specifically, means to use a luminance meter, by pressing against the first display and the second display, to measure the luminance values of the first display and the second display when the observed luminance of the two displays are the same.

Figure 3:
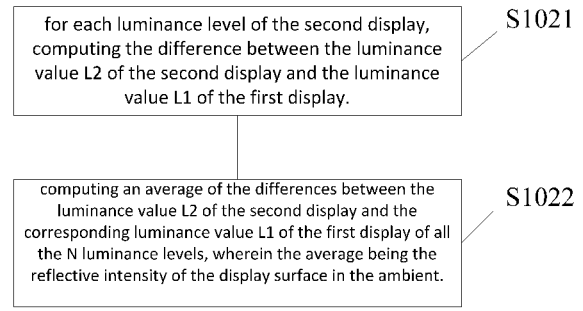
FIG. 3 is a flowchart of obtaining the reflective intensity of display surface in the ambient in the method for measuring reflective intensity of display surface according to the present invention.

Referring to FIG. 3, FIG. 3 is a flowchart of obtaining the reflective intensity of display surface in the ambient in the method for measuring reflective intensity of display surface according to the present invention, comprising the following steps.

Step S1021: for each luminance level of the second display, computing the difference between the luminance value L2 of the second display and the luminance value L1 of the first display.

At a luminance level of the second display, the luminance value of the second display is L2 and the corresponding luminance value of the first display is L1 when the two displays have the same observed luminance. Compute the difference L2−L1. The difference of the luminance value L2 of the second display and the corresponding luminance value L1 of the first display is computed for each of the N luminance levels of the second display.

Step 1022: computing an average of the differences between the luminance value L2 of the second display and the corresponding luminance value L1 of the first display of all the N luminance levels, wherein the average being the reflective intensity of the display surface in the ambient.

After computing the difference of the luminance value L2 of the second display and the corresponding luminance value L1 of the first display is computed for each of the N luminance levels of the second display, the total of all the differences are summed, and an average is computed. The average is the reflective intensity of the display surface in the ambient. The display surface in different bright ambient will have different reflective intensity. Furthermore, a plurality of measurements can be taken in a bright ambient to improve accuracy.

Figure 4:
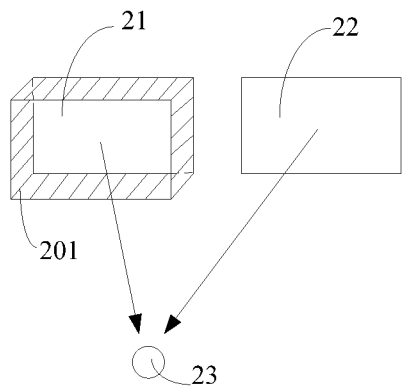
FIG. 4 is a schematic view showing the measurement of the reflective intensity of display surface according to the present invention.

As such, it should be noted that under the circumstance of the first display and the second display having the same observed luminance, the present invention obtains the luminance values of the first display and the second display placed in the same ambient, wherein the peripheral of the surface of the first display is surrounded by light-shielding object to effectively shield the ambient light to reduce or eliminate the effect on the measurement. Based on the luminance values of the first display and the second display, the present invention computes the reflective intensity of the display surface in the ambient. The present invention provides convenient and accurate means to measure the reflective intensity of the display surface Referring to FIG. 4, FIG. 4 is a schematic view showing the measurement of the reflective intensity of display surface according to the present invention. As shown in FIG. 4, the peripheral of the surface of the first display 21 is surrounded by light-shielding object 201, while the second display 22 is not surrounded by light-shielding object. The first display 21 and the second display 22 can be any known display, and the surfaces of the two displays are made of the same material. The first display 21 and the second display 22 are placed side by side in a bright ambient, such as, a bright ambient lit by fluorescent light or a bright office. The observed luminance can be the luminance perceived at a certain distance, such as, 2.5 m, in front of the first display 21 and the second display 22.

The light emitted from the first display 21 and the second display 22 arrives at a location 23, such as, human eye or equipment, at a specific distance in front of the displays. In idealistic situation, the luminance value of the first display 21 when displaying is not affected by the ambient light. In the present embodiment, the light-shielding objects 201 disposed surrounding the peripheral of the surface of the first display 21 can achieve the state of free of or near free of the effect of ambient light. On the other hand, the luminance value of the second display 22 when displaying is affected by the ambient light.

The luminance of the second display 22 is divided into N levels (N>1). At a luminance level of the N levels of the second display 22, the luminance of the first display 21 is adjusted so that the first display 21 and the second display 22 have the same observed luminance. By pressing the luminance meter against the surface of the first display 21 and the second display 22, the luminance values of the first display 21 and the second display 22 when displaying can be obtained. In other words, the step is to obtain the luminance value L2 of each luminance level of N levels of the second display 22 and the corresponding luminance value L1 of the first display 21 for each luminance level of the N levels of the second display 22 when the first display 21 and the second display 22 have the same observed luminance.

Then, the difference L2−L1 is computed. When the difference L2−L1 for each of the N levels of the second display 22 is computed, the average of all the differences is computed. The average is the reflective intensity of the display surface in the ambient.

Figure 5:
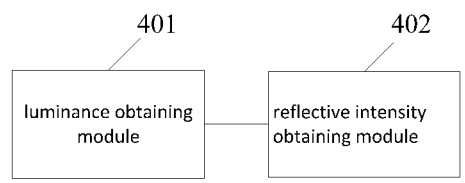
FIG. 5 is a schematic view showing the structure of an apparatus for measuring reflective intensity of display surface according to the present invention.

Referring to FIG. 5, FIG. 5 is a schematic view showing the structure of an apparatus for measuring reflective intensity of display surface according to the present invention, which comprises a luminance obtaining module 401 and a reflective intensity obtaining module 402.

The luminance obtaining module 401 is configured to obtain a luminance value of a first display and a luminance of a second display displaying in the same ambient wherein the first display and the second display have the same observed luminance, the peripheral of the surface of the first display is surrounded by light-shielding object, the first display and the second display are placed side by side.

In the present embodiment, the first display and the second display of the present invention can be displays of known display device. The observed luminance can be the luminance perceived by the human eye at a certain distance, for example, 2.5 m, in front of the first and the second display. The luminance obtaining module 401 is placed in the same ambient as the first display and the second display, with the first display and the second display side by side in a bright ambient, such as, an ambient lit by bright fluorescent light or in a bright office, and surrounding the peripheral of the display surface of the first display with light-shielding object, such as, light-shielding board, the effect of the ambient light can be effective reduced or eliminated. When the first display and the second display have the same observed luminance, the luminance value of the first display and the luminance value of the second display in the bright ambient are obtained.

The reflective intensity obtaining module 402 is configured to obtain the reflective intensity of the display surface in the ambient based on the luminance value of the first display and the luminance values of the second display when displaying.

Specifically, the reflective intensity obtaining module 402 is used in the bright ambient. According to the luminance values of the first display and the second display when displaying, the reflective intensity of the display surface in the bright ambient can be obtained.

Figure 6:
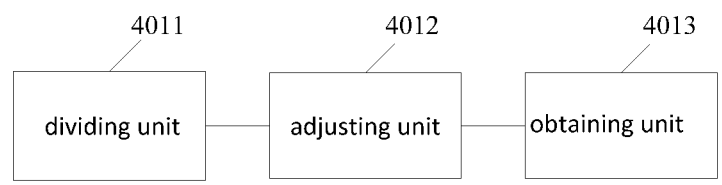
FIG. 6 is a schematic view showing the structure of an luminance obtaining module in the apparatus for measuring reflective intensity of display surface according to the present invention.

Referring to FIG. 6, the reflective intensity obtaining module of the present invention comprises a dividing unit 4011, an adjusting unit 4012 and an obtaining unit 4013.

The dividing unit 4011 is configured to divide the display luminance of the second display into N levels, wherein level 1 is the darkest and the level N is the brightest, and N is an integer greater than 1. Specifically, the grayscale of a typical display is 256 levels, with each grayscale level representing a different luminance level. The present invention does not impose any specific restriction on the division levels.

The adjusting unit 4012 is configured to adjust, at a luminance level of the N luminance levels of the second display, the display luminance of the first display so that the first display and the second display have the same observed luminance.

At a luminance level of the N luminance levels of the second display, adjust the display luminance of the first display and compare the display luminance of the two displays so that the first display and the second display have the same observed luminance. Because different materials have different reflectivity, the first display and the second display of the present embodiment are made of the same material.

The obtaining unit 4013 is configured to obtain a luminance value L2 for each of N luminance levels of the second display, and obtain a corresponding luminance value L1 of the first display when the first display and the second display have the same observed luminance.

Specifically, the obtaining unit 4012 is to obtain a luminance value L2 for each of N luminance levels of the second display and obtain a corresponding luminance value L1 of the first display when the first display and the second display have the same observed luminance, which means to use a luminance meter, by pressing against the first display and the second display, to measure the luminance values of the first display and the second display when the observed luminance of the two displays are the same.

Figure 7:
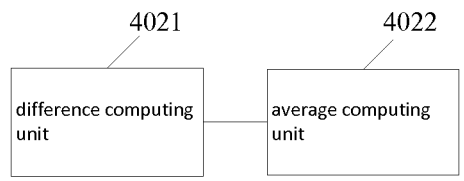
FIG. 7 is a schematic view showing the structure of an reflective intensity obtaining module in the apparatus for measuring reflective intensity of display surface according to the present invention.

Referring to FIG. 7, the reflective intensity obtaining module comprises: a difference computing unit 4021 and an average computing unit 4022.

The difference computing unit 4021 is configured to compute, for each luminance level of the second display, the difference between the luminance value L2 of the second display and the luminance value L1 of the first display.

The difference L2−L1 is computed for each luminance level of the N levels of the second display.

The average computing unit 4022 is configured to compute an average of the differences between the luminance value L2 of the second display and the corresponding luminance value L1 of the first display of all the N luminance levels, wherein the average is the reflective intensity of the display surface in the ambient.

Specifically, the average computing unit 4022 is for, after the difference L2−L1 for each of the N levels of the second display 22 is computed, computing the average of all the differences. The average is the reflective intensity of the display surface in the ambient.

As such, in the present invention, the peripheral of the surface of the first display is surrounded by light-shielding object to effectively shield the ambient light to reduce or eliminate the effect on the measurement so as to obtain the luminance value of the first display in the state of free of ambient light effect or near free of ambient light effect, and obtain the luminance of the second display in the same ambient under the effect of the ambient light. According to the division luminance levels, the present invention obtains the luminance values of the first display and the second display placed in the same ambient under the circumstance of the first display and the second display having the same observed luminance. Then, based on the luminance values of the first display and the second display, the present invention computes the reflective intensity of the display surface in the ambient. The present invention provides convenient and accurate means to measure the reflective intensity of the display surface without extra equipments and extra cost.

Embodiments of the present invention have been described, but not intending to impose any unduly constraint to the appended claims. Any modification of equivalent structure or equivalent process made according to the disclosure and drawings of the present invention, or any application thereof, directly or indirectly, to other related fields of technique, is considered encompassed in the scope of protection defined by the claims of the present invention.

What is claimed is:

1. A method for measuring reflective intensity of display surface, which comprises:
   placing a first display and a second display in the same ambient, dividing the display luminance of the second display into N levels, wherein N being an integer greater than 1, placing light-shielding object only to the first display to surround the peripheral of surface of the first display, the first display and the second display being placed side by side;

at a luminance level of the N luminance levels of the second display, adjusting the display luminance of the first display so that the first display and the second display are perceived by the human eye distant from and in front of the first display and the second display as having the same observed luminance;

obtaining a luminance value L2 for each of N luminance levels of the second display measured by a luminance measuring device such as luminance meter, and obtaining a corresponding luminance value L1 of the first display measured by a luminance measuring device such as luminance meter, when the first display and the second display are perceived by the human eye as having the same observed luminance;

obtaining the reflective intensity of the display surface in the ambient based on a difference between the measured luminance value L1 of the first display and the measured luminance values L2 of the second display when displaying.

2. The method as claimed in claim 1, characterized in that the step of obtaining the reflective intensity of the display surface in the ambient based on the measured luminance value L1 of the first display and the measured luminance values L2 of the second display when displaying further comprises:

for each luminance level of the second display, computing the difference between the luminance value L2 of the second display and the luminance value L1 of the first display; and computing an average of the differences between the luminance value L2 of the second display and the corresponding luminance value L1 of the first display of all the N luminance levels, wherein the average is used as the reflective intensity of the display surface in the ambient.

3. The method as claimed in claim 1, characterized in that the surface of the first display and the surface of the second display are made of the same material.

4. A method for measuring reflective intensity of display surface, which comprises:

obtaining a measured luminance value of a first display and a measured luminance value of a second display when the first display and the second display displaying under the condition of the first display and the second display being perceived by the human eye distant from and in front of the first display and the second display as having the same observed luminance, placing light-shielding object only to the first display to surround the peripheral of surface of the first display, the first display and the second display being placed side by side; and obtaining the reflective intensity of the display surface in the ambient based on a difference between the measured luminance value of the first display and the measured luminance values of the second display when displaying.

5. The method as claimed in claim 4, characterized in that the step of obtaining a measured luminance value of a first display and a measured luminance value of a second display when the first display and the second display displaying further comprises:

dividing the display luminance of the second display into N levels, wherein N being an integer greater than 1;

at a luminance level of the N luminance levels of the second display, adjusting the display luminance of the first display so that the first display and the second display are perceived by the human eye as having the same observed luminance; and obtaining a luminance value L2 for each of N luminance levels of the second display measured by a luminance measuring device such as luminance meter and obtaining a corresponding luminance value L1 of the first display measured by a luminance measuring device such as luminance meter, when the first display and the second display are perceived by the human eye as having the same observed luminance.

6. The method as claimed in claim 5, characterized in that the step of obtaining the reflective intensity of the display surface in the ambient based on a difference between the measured luminance value of the first display and the measured luminance values of the second display when displaying further comprises:

for each luminance level of the second display, computing the difference between the luminance value L2 of the second display and the luminance value L1 of the first display; and computing an average of the differences between the luminance value L2 of the second display and the corresponding luminance value L1 of the first display of all the N luminance levels, wherein the average is used as the reflective intensity of the display surface in the ambient.

7. The method as claimed in claim 4, characterized in that the surface of the first display and the surface of the second display are made of the same material.

8. An apparatus for measuring the reflective intensity of display surface, which comprises:

a luminance obtaining module, configured to obtain a measured luminance value of a first display and a measured luminance of a second display displaying in the same ambient wherein under the condition of the first display and the second display perceived by the human eye distant from and in front of the first display and the second display as having the same observed luminance, placing light-shielding object only to the first display to surround the peripheral of surface of the first display, the first display and the second display being placed side by side; and a reflective intensity obtaining module, configured to obtain the reflective intensity of the display surface in the ambient based on a difference between the measured luminance value of the first display and the measured luminance values of the second display when displaying.

9. The apparatus as claimed in claim 8, characterized in that the luminance obtaining module further comprises:

a dividing unit, configured to divide the display luminance of the second display into N levels, wherein N being an integer greater than 1;

an adjusting unit, configured to adjust, at a luminance level of the N luminance levels of the second display, the display luminance of the first display so that the first display and the second display are perceived by the human eye as having the same observed luminance; and an obtaining unit, configured to obtain a luminance value L2 for each of N luminance levels of the second display measured by a luminance measuring device such as luminance meter and obtain a corresponding luminance value L1 of the first display measured by a luminance measuring device such as luminance meter, when the first display and the second display are perceived by the human eye as having the same observed luminance.

10. The apparatus as claimed in claim 9, characterized in that the reflective intensity obtaining module comprises:
- a difference computing unit, configured to compute, for each luminance level of the second display, the difference between the luminance value L2 of the second display and the luminance value L1 of the first display; and
- an average computing unit, configured to compute an average of the differences between the luminance value L2 of the second display and the corresponding luminance value L1 of the first display of all the N luminance levels, wherein the average being the reflective intensity of the display surface in the ambient.

11. The apparatus as claimed in claim 8, characterized in that the surface of the first display and the surface of the second display are made of the same material.

* * * * *